United States Patent [19]
Kroll

[11] Patent Number: 5,861,006
[45] Date of Patent: Jan. 19, 1999

[54] SYSTEM FOR SELECTIVELY REFORMING AN ICD

[75] Inventor: Mark W. Kroll, Simi Valley, Calif.

[73] Assignee: Angeion Corporation, Brooklyn Park, Minn.

[21] Appl. No.: 749,441

[22] Filed: Nov. 15, 1996

[51] Int. Cl.[6] .................................................. A61N 1/39
[52] U.S. Cl. .................................................... 607/5
[58] Field of Search ............................. 607/5, 7, 27, 29, 607/34

[56] References Cited

U.S. PATENT DOCUMENTS

| | | | |
|---|---|---|---|
| 5,312,444 | 5/1994 | Bocek et al. | 607/5 |
| 5,350,405 | 9/1994 | Silvian | 607/27 X |

Primary Examiner—Jeffrey R. Jastrzab
Attorney, Agent, or Firm—Brad Pedersen

[57] ABSTRACT

An implantable cardioverter defibrillator (ICD) in which capacitor systems are automatically reformed using a software-implemented computer system. The charge history and performance of the capacitor system are measured to perform intelligent calculations and to set the automatic capacitor reforming cycle. Individual capacitors among a group of many are isolatively charged as needed. Moreover, a sub optimal charge is used to automatically reform the capacitors to efficiently use battery energy. Further, excess charge is directed from one capacitor to another to thereby conserve energy. Specifically, the disclosure relates to an autonomous capacitor charging system which enhances ICD reliability to sustain real time provision of high current pulses.

30 Claims, 4 Drawing Sheets

SYSTEM FOR SELECTIVELY REFORMING AN ICD

RELATED APPLICATIONS

The present invention is related to two co-pending applications. The first is a U.S. patent application filed on Oct. 27, 1995, entitled "AUTOMATIC CAPACITOR MAINTENANCE FOR AN ICD", Ser. No. 08/549,284. The second is a U.S. patent application filed on Mar. 20, 1996, entitled "AUTOMATIC CAPACITOR MAINTENANCE FOR AN ICD", Ser. No. 08/620,390. Both of these applications are assigned to the assignee of the present invention and the disclosure of each application is hereby incorporated by reference.

FIELD OF THE INVENTION

The present invention relates to implantable cardioverter defibrillator (ICD) devices. More particularly, the present invention pertains to a system for selectively reforming the high voltage output systems of an ICD based on the charge history and charge performance of the battery and capacitor systems so as to maintain charge performance while conserving battery power.

BACKGROUND OF THE INVENTION

The implementation and use of high voltage output systems within implantable cardioverter defibrillator (ICD) devices is well known. In order to generate the high voltage output necessary for effective defibrillation countershocks, a low voltage, high current battery system is connected via a transformer to a high voltage capacitor system. When a cardiac arrhythmia is detected by the ICD, the battery system quickly charges the capacitor system so that a high voltage defibrillation countershock can be delivered by the device. An example of the high voltage output system for an existing ICD device is described in U.S. Pat. Nos. 5,404,363 and 5,372,605.

Generally, ICD devices have high voltage capacitor systems comprised of aluminum electrolytic capacitors and high current battery systems comprised of silver vanadium oxide (SVO) battery cells. Although aluminum electrolytic capacitors have a relatively high energy density per volume, these type of capacitors tend to degrade electrochemically over time thereby increasing the charge time required to fully charge the capacitor system. The SVO battery cells also have a tendency to degrade electrochemically over time due to the increased equivalent series resistance (ESR) within the battery which decreases the current output capabilities of the battery.

The conventional solution to both of these problems has been to conduct a periodic reforming of the high voltage output system of an ICD by charging the capacitor system to its full rated voltage and then allowing that voltage to slowly trickle off. In this way, both the high current battery system and the high voltage capacitor system are exercised so as to reform the electrochemistries of each system, thereby reducing the impact on charge performance and component life due to electrochemical degradation over time. Originally, this reforming process was accomplished manually by having a patient visit the physician every two to three months, at which time the physician would program the ICD to charge, but not deliver, a full voltage rated countershock. Presently, the reforming of the high voltage output system is accomplished automatically by the ICD based on a fixed time period (e.g., every month, every six months), at the end of which a full charge cycle of the capacitor system is automatically conducted. While this kind of simple periodic reform cycle was more than effective for early ICD devices where the life span of the device was typically less than three years and the battery budget could easily support the periodic reform cycles, newer ICD devices are smaller and have much longer life spans. An example of such an ICD which is used as a prophylactic device is described in U.S. Pat. No. 5,439,482. In these newer designs for an ICD, battery power is at more of a premium than in previous designs and the periodic reforming of the high voltage output system can represent a significant portion of the battery budget over the life of the device.

Two alternate techniques for accomplishing reforming of the battery system and the capacitor system are disclosed in the previously-identified co-pending applications. In the first application entitled "AUTOMATIC CAPACITOR MAINTENANCE FOR AN ICD", a technique is disclosed for measuring the leakage current of the capacitor system at a relatively low voltage and using this value to estimate whether the capacitor system needs to be reformed. By utilizing a low voltage test process, battery power is conserved and full voltage reforming is conducting only when it is determined that the capacitor is in need of reforming. In the second application entitled "AUTOMATIC BATTERY MAINTENANCE FOR AN ICD", a technique is disclosed for measuring an electrical parameter of the battery system and using this value to determine whether the battery system needs to be reformed. Again, battery power is conserved by only performing a full voltage reform when it is determined that the internal resistance of the battery system has increased to the point where charge performance is degraded. While each of these inventions represent a significant improvement over the existing periodic reform technique, both of these inventions suffer from the disadvantage of potentially requiring additional circuitry within the ICD in order to implement the invention.

Although existing techniques for reforming the high voltage output system of an ICD are adequate for current ICD systems, it would be advantageous to develop a more efficient reform system for the high voltage output system of an ICD. It would also be advantageous to develop a reform system that did not require significant additional circuitry within the ICD.

SUMMARY OF THE INVENTION

The present invention provides a system for selectively reforming the high voltage output systems of an ICD based on the charge history and charge performance of the battery and capacitor systems so as to maintain charge performance while conserving battery power. The system is preferably implemented in a microprocessor within the ICD which measures the charge history and charge performance of the high voltage output system of the ICD and periodically determines an estimated charge time based on these parameters. If the estimated charge time is greater than a predetermined value, a reform process is initiated. In a preferred embodiment, the reform process is a soft reform that utilizes lower voltage and frequency values so as to further conserve battery power during the reform process. In an alternate embodiment, the reform process includes circuitry to allow multiple capacitors within the capacitor system to be reformed individually, and can utilize the reform charge from one capacitor to aid in reforming another capacitor.

By monitoring the charge history and charge performance of the high voltage output system of the ICD, the present invention conserves valuable battery energy by only performing the reform process when actually needed, and further by performing only such reform as is actually needed. In a conventional ICD which utilizes a monthly reform, an energy equivalent to more than 80 countershocks is consumed simply in keeping the battery and capacitor systems reformed. By decreasing this energy requirement, the present invention optimizes the life and capacity of the device, without the necessity of additional circuitry.

DESCRIPTION OF THE PREFERRED EMBODIMENT

Figure 1:
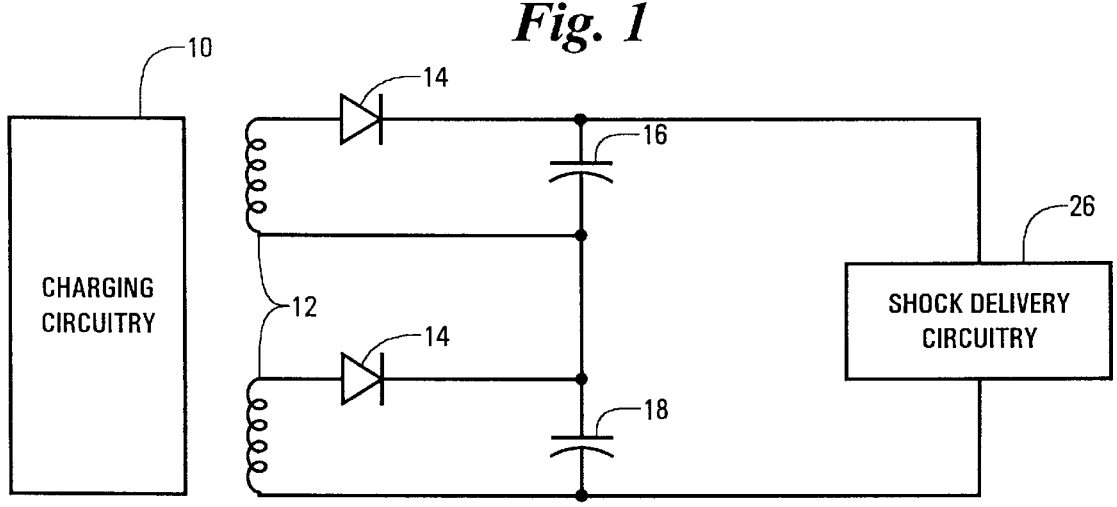
FIG. 1 is a simplified representation of a circuit for a conventional ICD.

Referring now to the drawings, and in particular to FIG. 1, a simplified version of a typical ICD is presented. The charging circuit 10 charges through a flyback transformer secondary 12 to generate a high voltage output. Diodes 14 steer the high voltage and store it in capacitor system 16 and capacitor system 18. The capacitor systems 16 and 18 are discharged through shock delivery circuit 26. Preferably, shock delivery circuit 26 includes a pair of electrodes connected to the heart of a human patient to discharge high voltage to defibrillate the heart. For a more detailed description of the design and operation of an ICD, reference is made to U.S. Pat. No. 5,404,363 which is incorporated herein by reference.

Figure 2:
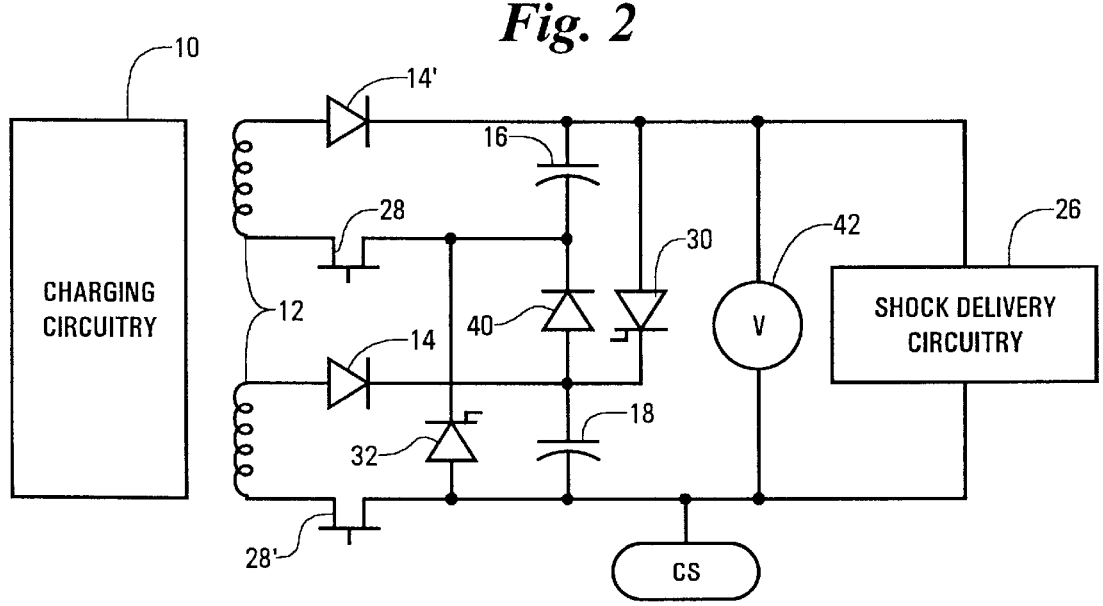
FIG. 2 is a circuit diagram shown the essential elements of the present invention.

The principle circuit elements of the present invention are shown in detail in FIG. 2. The circuit includes charge circuit 10, flyback transformer secondary 12 and diodes 14 with shock delivery circuit 26. Field Effect Transistor (FET) switches 28 and 28'control the distribution of charge energy, as will be discussed herein later. Silicon Controlled Rectifier (SCR) switches 30 and 32 isolate capacitor systems 16 and 18 from each other, respectively. Conventional diode 40 is a rectifier. Voltmeter 42 is connected across the terminals of shock delivery circuit 26 and is used to monitor the voltage across the terminals. Control system, CS, is operatively connected to the circuit as shown. The CS is preferably a microprocessor directed by an algorithmic software to implement the present invention.

Figure 3:
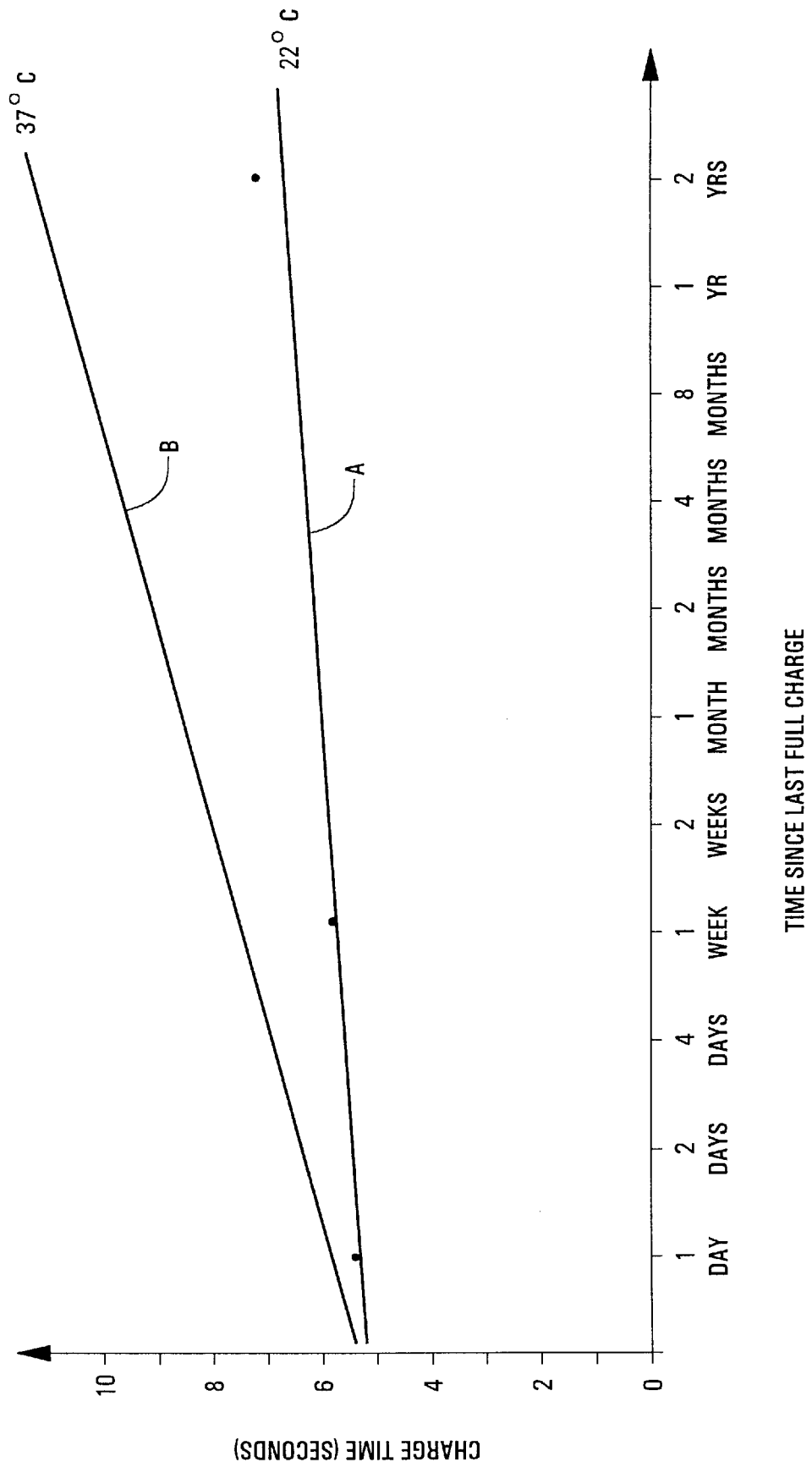
FIG. 3 is a graphical representation showing increments in charge time, for a typical capacitor, as a function of time since the last full charge.

FIG. 3 shows the increase in charge time, for a typical capacitor system, as a function of the time since its last full charge. This is an inverse exponential relationship and is shown on a logarithmic x-axis. The relationship shown in curve A is one of the parameters used in the algorithm of the present invention to estimate the performance of the capacitor system and the optimum remedial schedule to reform the capacitor system.

Figure 4:
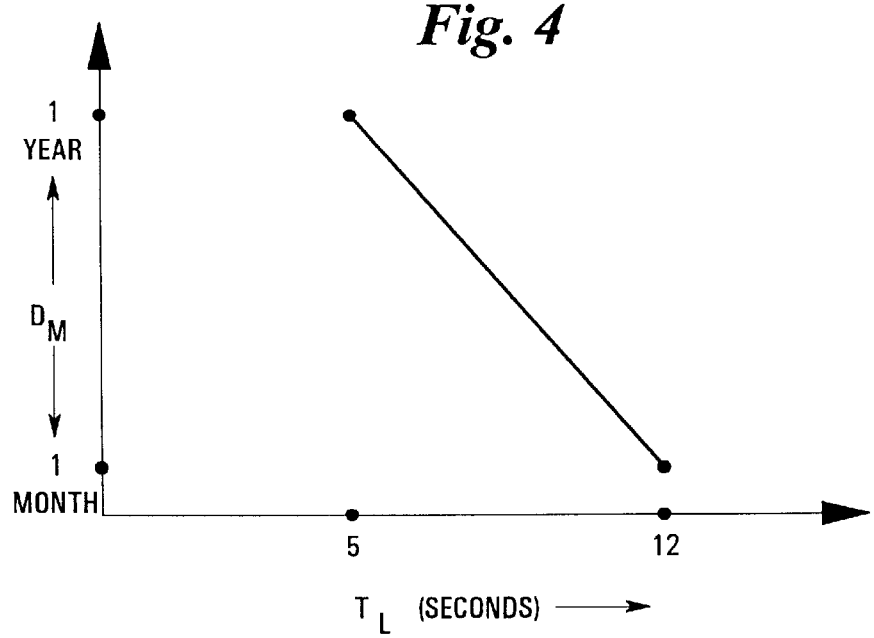
FIG. 4 is a graphical representation of the relationship between delay to mandatory reform time ($D_M$) and last (most recent) charge time $T_L$.

FIG. 4 shows a simplified linear relationship between reforming time and charge time. The charge time is used to determine the delay to mandatory reform time ($D_M$). The $D_M$ is one of the important parameters of the present invention which indicates the capacitor system's conditions and also provides the combined capability status of the capacitor system and the battery. The (last) most recent charge time is designated $T_L$.

Figure 5:
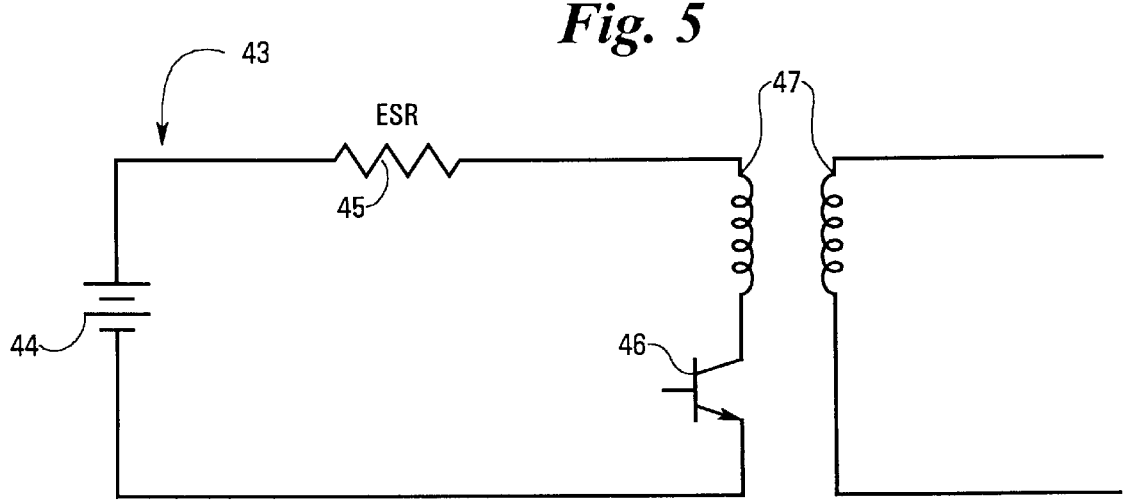
FIG. 5 is a diagram of a soft reform circuit.

FIG. 5 shows a circuit 43, a battery system 44, equivalent series resistance (ESR) 45, invertor 46 and transformer 47. This is an equivalent circuit which is used to explain the soft or a slow reform of the capacitor system to conserve energy. The ESR represents the internal resistance of a battery cell which causes its loaded voltage to be less than the open circuit voltage. A high battery ESR indicates a reduction in output current and thereby renders the ICD unreliable because the power supply will not sustain the provision of high current pulses. Periodic capacitor charging limits the development of ESR. Accordingly, the soft reform regimen provides the advantage of minimizing the energy waste in the ESR.

In the present invention, invertor 46 is operated in a manner (lower duty cyclethat limits the power consumption from the battery system 44 and enables the implementation of a soft reform regimen. The reforming cycle of the present invention is performed by the software, disclosed in FIG. 6, which directs control system "CS". Starting with logic step or block 50 the software program is initiated by calculating $D_M$ from $T_L$. Consecutive steps and subroutines comprise the algorithm which performs intelligent calculations to automatically monitor the relevant perimeters in order to reform the capacitor system as needed.

As will be discussed hereinbelow, the present invention discloses a method and apparatus to reform capacitors based on intelligent analysis of the parameters relating to charge history and performance of a system of capacitors. Further, individual capacitors are reformed separately while battery energy is efficiently used in the reforming process. Thus, a real-time and continuous monitoring and reforming of the capacitor system in conjunction with conversation of battery energy is implemented to provide a reliable and ever-ready ICD system.

Figure 6:
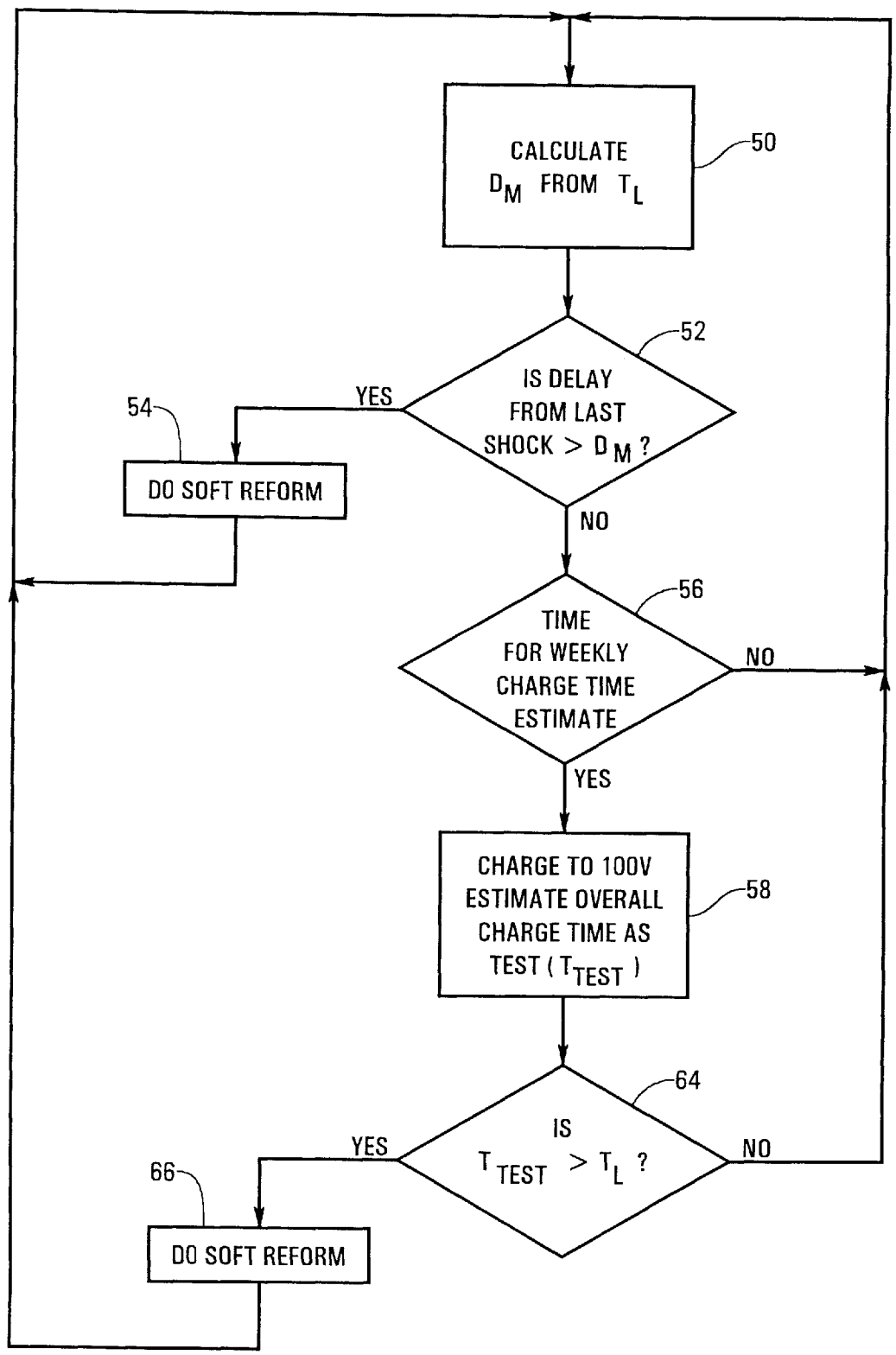
FIG. 6 is a flow chart showing algorithmic logic steps of the present invention.

Referring now to FIGS. 1–5 in light of the algorithm disclosed in FIG. 6, the present invention is initiated by calculating the delay to mandatory reform time ($D_M$) from the (last) most recent charge time ($T_L$) under block 50 (See FIG. 6). The routine proceeds to decision block 52 wherein the delay from the last shock ($D_S$) is compared against the calculated $D_M$. If $D_S$ is greater than $D_M$ the subroutine proceeds to block 54 to perform a soft reform. From block 54, the subroutine reverts back to block 50 to execute calculations as needed. It is significant to note that the calculations performed under block 50 are particularly based on the disclosures of FIGS. 3 and 4. FIG. 3 shows the increase in charge time for a typical capacitor as a function of the time since the last full charge. The relationship between the variables (charge time and time since last full charge) is inverse exponentially and this relationship is shown based on a logarithmic x-axis. Curve A shows observations based over a two year period with the charge time increasing from 5 seconds to about 7.5 second. This increase will not be clinically significant for most patients, However, many capacitors exhibit significantly higher rates of charge time increase. Curve A is derived from bench testing a capacitor at 22 degrees Celsius. Curve B is obtained from data of characteristic depletion of capacitors in the human body at 37 degrees Celsius. It is clearly evident from curves A and B that capacitors in human implanted ICDs could have a higher rate of depletion and would need more frequent reforming.

Furthermore, the disclosure in FIG. 4 shows a simplified linear relationship for an algorithm to estimate the next time the capacitor systems 16 and 18 will need reforming. In the horizontal axis we observe a (last) most recent charge time ($T_L$) of 5 seconds. This suggests that the capacitor and battery combination are both very well maintained. Based on this data a one year period would be allowed for the delay to mandatory reform time ($D_M$). On the other hand, another most recent charge time ($T_L$) is shown as 12 seconds. If the capacitors were to have a 12 second charge time, it would indicate that the capacitor systems 16 and 18 have depleted significantly since the last charge and that the capacitor systems 16 and 18, and or the battery system are in less than optimal state of charge conditions. Realizing this, the calculated delay to mandatory reform time (DM) would be one month. The interpolation for values between the 5 second and 12 seconds is based on a logarithmic scale for the vertical axis.

Referring now to FIG. 6, the calculation under block 50 could be based on a certain DM, for example three months, from the previous shock. The curve developed in FIG. 4 assumes a "hard charge" which is using a maximum charge rate. However, the algorithm of FIG. 6 reverts to a soft reform if delay form last shock ($D_S$), is greater than $D_M$. Further, under decision block 52 if $D_S$ is less than or equal to $D_M$, the algorithm proceeds to decision block 56 to check it is time for a weekly charge time estimate. If it is time, the routine proceeds to block 58 where all or any one of the capacitor systems are charged to a minimum voltage, for example 100 v. If not, the routine proceeds back to block 50 to perform the calculations as indicated. Under block 58 the overall charge time is estimated as a test time ($T_{TEST}$). Hereafter, when the maximum charge voltage is reached in block 58, the software program proceeds to decision block 64 where the estimated $T_{TEST}$ of block 58 is compared against a set time limit. Therefore, under decision block 64 if $T_{TEST}$ is greater than the set time limit, the subroutine precedes to perform a soft reform under block 66. On the other hand, if the estimated $T_{TEST}$ is less than or equal to the set limit, the routine precedes to block 50 to perform calculations as indicated.

Generally the operations of the present invention include, calculating $D_M$ from $T_L$. On a predetermined time interval basis $D_M$ is compared with $D_S$. In the preferred embodiment this comparison is made on a daily basis. If $D_S$ is greater than $D_M$, then a 'soft' reform is executed and a timer is reset to zero at the end of the reform. If $D_S$ is equal to or less than $D_M$ then the algorithm confirms if it is time to perform a weekly charge time estimate. If it is time, one or all of the capacitor systems are charged to a minimum voltage, for example 100 volts. The charge time is noted precisely. This charge time is then used to estimate the overall charge time as T TEST which would be required for a maximum energy shock. The empirical estimation formula is derived from the following equation: Full charge time=$(V^2_{MAX}/V^2_{TEST})$ $T_{TEST}$ where $T_{TEST}$ in this equation is the test voltage charge time. For example if the maximum voltage is 750 V and the test voltage is 100 $V_{TEST}$, the ratio, i.e, 7.5 would be squared to yield a correction ratio of 56.25. This quantity will be multiplied by $T_{TEST}$, the test voltage charge time required for the 100 $V_{TEST}$, to come up with an estimate for the full charge time. Thus, if the test voltage charge time for the 100 V is 100 ms, the full charge time will be 5.625 seconds.

The advantages of using a low voltage full charge time such as the 5.625 seconds is that it incorporates the most important capacitor depletion parameters which include battery internal impedance and increase in capacitor leakage. The present invention enables to monitor these critical parameters by using a charge as low as 100 volts which requires only about one joule of energy in a typical ICD system. Accordingly, the tests performed by the method and device of the present invention may be scheduled to be performed on a weekly basis and consume energy of about 52 joules per year.

As discussed hereinabove, if $T_{TEST}$ is greater than the predetermined limit, then a soft reform is executed. Referring to FIG. 4, the method and device for soft reforming include the inverter 46 which is run at a very low rate such that less than one third of the power that is normally used to charge a capacitor for emergency shock delivery is consumed. This approach reduces the amount of energy consumed to about one half of what is normally required to totally reform the capacitor system. The prior art method of reforming capacitors which is referred to as a "hard charge" involves rapidly charging the capacitor system to deliver the shock. In order to accomplish this, the battery 44 and the invertor 46 are run at maximum power transfer. Accordingly, the battery voltage is drawn down to about half its normal voltage. While this results in a very rapid power transfer, it has the undesirable side effect of wasting about one half of the battery energy internally. This is because the equivalent series resistance (ESR) 45 of the battery is in the order of about one ohm. Thus, the losses can be fairly significant when a capacitor system is charged using the "hard charge" approach.

The present invention provides a unique circuit designed to reform the capacitor systems 16 and 18 using the most economical battery energy. Referring now to FIG. 2, FET switches 28 to 28' are used to control current flow into capacitor systems 16 and 18, respectively. The FET switches 28 and 28' operate in an enhanced mode which means that no current flows when zero gate voltage is applied and increasing the gate voltage increases the current. Therefore, to commence the reforming operation of capacitor system 16, for example, FET switch 28 is turned on and FET switch 28' is turned off. This allows the charging energy to go to only capacitor system 16 and prevents current from flowing to capacitor system 18. Similarly, if it is required to reform capacitor system 18, FET switch 28' is turned on and FET switch 28 is turned off thus preventing current from flowing to capacitor system 16.

Accordingly, the circuitry of the present invention provides the added advantage and option to charge a specific group of capacitor systems of an ICD. Allowing the charging energy to be directed to capacitor system 16, for example, enables to conserve battery energy by reforming only the capacitor system which needs reforming. Further, the present invention enables the energy from one capacitor system to jump start the other capacitor system. Specifically, for example, after capacitor system 16 is fully charged and reformed then SCR switches 30 and 32 are turned on and the charge from capacitor system 16 is thus shared with the capacitor system 18. It should be noted that SCR switches 30 and 32 are silicon diodes with an additional electrode or a gate. If a bias voltage is applied to the gate to keep it at or near the same potential as the cathode of the diode, the SCR behaves as if working with reverse voltage with both directions of applied voltage, a small leakage current will flow. If the gate is biased to be more positive than the cathode, the SCR behaves as a conventional diode. Therefore, the gate can be used to turn the SCR on thus enabling forward current to be controlled.

In the preferred embodiment, when a capacitor system is fully charged the excess charge can be directed to the next capacitor system. In the prior art, this excess energy was trickled off and wasted thus contributing to an ever increasing energy demand o the battery system. For illustration purposes, assuming capacitor system 16 to be fully charged and carrying an excess charge, then SCR switches 30 and 32 are turned on and the excess charge from capacitor system 16 is directed to capacitor system 18. Because of losses in the sharing process of the excess charge between the capacitor system, the charge of capacitor system 18 may not be brought to a full level. However, the amount of energy to then reform capacitor system 18 to its full capacity is reduced by the amount transferred from the excess charge and this in turn reduces the energy requirement on the battery therefore yielding longer battery life and enhancing the reliability of the ICD system.

Having thus described the preferred embodiments of the present invention, those skilled in the are will readily appreciate the many other embodiments which can be employed within the scope of the claims provided below.

What is claimed is:

1. An improved implantable cardioverter defibrillator (ICD) system having at least one capacitor system which is charged from a battery system by control circuitry integrated within the ICD to deliver an electrical countershock in response to detection of a cardiac dysrhythmia in which the at least one capacitor system is automatically reformed using a control system to make intelligent calculations of the charge history and performance of the at least one capacitor system, the improvement comprising:

means for measuring the charge history and performance of the at least one capacitor system;

means for automatically calculating charge time based on said charge history and performance of the at least capacitor system; and means for charging and monitoring the at least one capacitor system based on said charge time;

said means for measuring, said means for automatically calculating charge time and said means for charging and monitoring the at least one capacitor system being in electrical communication with the control circuit in the ICD system.

2. The improved ICD system of claim 1 wherein said means for automatically measuring the charge history and performance of the at least one capacitor system includes a software system directing computer system as part of the control circuitry of the ICD.

3. The improved ICD system of claim 1 wherein said means for automatically calculating said charge time based on said charge history and performance of the at least one capacitor system includes a software system integrated with the control circuit in the ICD system.

4. A software-directed system in cooperation with a control circuit of an implantable cardioverter defibrillator (ICD) device to automatically reform capacitor systems in the ICD device which are charged from a battery system by the control circuit to deliver an electrical countershock in response to detection of a cardiac dysrhythmia, the software-directed system comprising:

means for calculating capacitor performance and charge history based on delay to mandatory reform time ($D_M$) and most recent charge time ($T_L$);

means for calculating delay from last shock time ($D_S$);

means for performing a soft reform;

means for estimating charge time on a preset time interval basis;

means for charging to 100 V to estimate overall charge time as Test ($T_{TEST}$); and means for comparing said charge time as test with said most recent charge time ($T_L$);

said means for calculating capacitor performance anal charge history, said means for calculating delay from last shock time, said means for performing a soft reform, said means for estimating charge time, said means for charging to 100 volts and said means for comparing having electrical communication therebetween and further being in operative electrical communication with the control circuit of the ICD device.

5. The system according to claim 4 wherein said means for calculating capacitor performance and charge history includes a computer system under the direction of said software and in electrical communication with the control circuit of the ICD device.

6. An implantable cardioverter defibrillator (ICD) device in which capacitor systems charged from a battery system through an invertor by a control circuit to deliver an electrical countershock in response to detection of a cardiac dysrhythmia are automatically reformed using a low frequency charging power through the invertor wherein a software implemented computer system that is part of the control circuit of the ICD provides intelligent calculations to control the automatic reforming, the software-implemented computer system comprising:

means for automatically calculating charge time based on charge history and performance of the capacitor systems;

means for charging and monitoring the capacitor systems based on said charge time; and circuit means for implementing a soft reform to operate the invertor at said low frequency;

said means for automatically calculating, said means for charging and said circuit means for implementing a soft reform being in electrical communication with each other and integrated with said ICD device.

7. The software implemented computer system of claim 6 wherein said means for charging and monitoring includes FET switches to direct current from one capacitor to another in said capacitor systems.

8. The software-implemented computer system of claim 6 wherein said means for charging and monitoring includes SCR switches which direct excess current from one capacitor to another in said capacitor systems.

9. The software implemented computer system of claim 6 wherein said circuit means for implementing a soft reform includes a battery system connected in series to a resistor having a resistance equal to an equivalent series resistance (ESR) of said battery system.

10. An implantable cardioverter defibrillator (ICD) device having a software implemented computer system wherein capacitor systems charged from a battery system by a control circuit to deliver an electrical countershock in response to detection of a cardiac dysrhythmia are automatically reformed using a limited amount of battery energy to deliver a maximum shock to a patient in whom the ICD device is implanted, the software implemented computer system comprising:

means for monitoring a charge time;

means for estimating reforming needs from said charge time to a sub maximal shock;

means for charging to 100 volts wherein overall charge time is set as test;

means for comparing said charge time as test with a last charge time; and means for performing a soft reform;

said means for monitoring, said means for estimating, said means for charging, said means for comparing and said means for performing a soft reform being in electrical communication with said ICD device and being directed by said software implemented computer system.

11. The system of claim 10 wherein said means for performing a soft reform includes a circuit having a battery system, a resistor and an invertor.

12. The system of claim 10 wherein said means for charging to 100 volts includes a voltmeter to regulate said charging to 100 volt.

13. An implantable cardioverter defibrillator (ICD) device including at least one capacitor system charged from a battery system by a control circuit to deliver an electrical countershock in response to detection of a cardiac dysrhythmia, the ICD device also including a software system to automatically reform the at least one capacitor system in the ICD wherein delay between consecutive reforms is based on intelligent calculations executed by the software system such that an autonomous reforming cycle is used instead of a fixed time, the device comprising:
    a computer directed by said software system to perform an automatic reform of the at least one capacitor system;
    circuit means for performing a soft reform directed by said software system;
    means for initiating said soft reform; and
    means for terminating said soft reform;
    said soft reform being autonomously performed based on preset parameters, of performance and charge history of the at least one capacitor system, which said software system utilizes to execute said intelligent calculations to perform said autonomous reforming cycle.

14. The device according to claim 13 wherein said circuit means for performing a soft reform includes a battery system connected in series to a resistor having a resistance equal to an ESR of said battery system.

15. The device according to claim 13 wherein said means for initiating and said means for terminating include a voltmeter to activate said initiating means and said terminating means based on a voltage reading of said capacitor systems.

16. An implantable cardioverter defibrillator (ICD) device including a capacitor system having at least two capacitors charged from a battery system by a control circuit to deliver an electrical countershock in response to detection of a cardiac dysrhythmia is integrated with a circuit isolation device including a software implemented computer system to automatically reform the capacitor system within the ICD device wherein a capacitor, in the capacitor system, is isolatively reformed based on intelligent calculations wherein excess charge from the reformed capacitor is directed to jump start another capacitor such that the amount of energy required to fully charge said another capacitor is reduced by the amount of said excess charge transferred to said another capacitor, the circuit isolation device comprising;
    means for performing the automatic reform;
    a plurality of FET switches; and
    a plurality of SCR switches;
    said means for performing the automatic reform, said FET switches and said SCR switches having electrical communications therebetween and being integrated with a control circuit in the ICD device.

17. The device according to claim 16 wherein said FET switches are connected to said capacitor system to direct current to only a selected capacitor in said capacitor system.

18. The device according to claim 16 wherein said SCR switches are connected to said capacitor system to direct excess current from a fully charged capacitor to another capacitor in said capacitor system.

19. An implantable cardioverter defibrillator (ICD) integrated with an automatic capacitor charging device to form an autonomous capacitor reforming system wherein capacitors in the ICD are reformed based on intelligent calculations, the capacitor reforming system comprising:
    the ICD including:
        a converter section;
        a flyback charging switch;
        at least one capacitor; and
        a control circuit;
            said converter section, said flyback charging switch, said at least one capacitor and said control circuit being in electrical communication and comprising electronic components of said ICD;
    the automatic capacitor charging device comprising:
        a circuit including: a plurality of FET switches, a plurality of SCR switches, and connection means for connecting said circuit to said ICD;
        a computer system;
        a soft reform circuit including:
            an invertor, and
            a resistor calibrated at an ESR of a battery system in said invertor;
        wherein said ICD, said capacitor reforming system, said computer system, and said soft reform circuit being in operative and electrical communication with each other and comprising said autonomous capacitor reforming system.

20. The capacitor reforming system of claim 19 wherein said control circuit includes a voltmeter to monitor voltage readings of the capacitor reforming system.

21. The capacitor reforming system of claim 19 wherein said computer system includes a software directing said computer system to make intelligent calculations and operate the capacitor reforming system.

22. A method to automatically charge a capacitor system in an implantable cardioverter defibrillator (ICD) device wherein a reforming system in cooperation with said ICD device forms an autonomous reforming system based on intelligent calculations performed by a software implemented computer system to reform the capacitor system based on charge and performance history comprising the autonomous reforming system implemented step of:
    (a) calculating a mandatory reform time (DM) from a most recent charging time (TL);
    (b) comparing said DM with a delay from a last shock (DS);
    (c) performing a soft reform if said DS is greater then said DM;
    (d) checking if it is time for a weekly charge time estimate;
    (e) charging the capacitor system to a minimum voltage if it is time for said weekly charge time estimate;
    (f) comparing said weekly charge time estimate with a set time limit;
    (g) performing a soft reform if said weekly charge time estimate is greater than said set time limit; and
    (h) resetting back to step (a) after one of said step of performing a soft reform, said step of checking if it is time for a weekly charge time estimate and said step of comparing said weekly charge time estimate.

23. The method according to claim 22 wherein said step of performing a soft reform includes running an invertor at a low frequency to conserve batter energy.

24. The method according to claim 22 wherein said step of charging the capacitor system to a minimum voltage includes charging to 100 V to estimate overall charge time as test.

25. An implantable cardioverter defibrillator (ICD) comprising at least one high voltage capacitor system which is charged from a battery system by control circuitry integrated within the ICD to deliver an electrical countershock in response to detection of a cardiac dysrhythmia, the at least one capacitor system being automatically reformed by a system within the ICD that measures the charge history and performance of the at least one capacitor system and automatically calculates an estimated charge time based on said charge history and performance of the at least one capacitor system and initiates charging and monitoring of the at least one capacitor system based on said estimated charge time.

26. The ICD of claim 25 wherein the system for automatically reforming the at least one capacitor system calculates a mandatory reform time based on a most recent charging time and compares the mandatory reform time to a delay measured from a last countershock and initiating a reform of the at least one capacitor system if the delay is greater than the mandatory reform time.

27. The ICD of claim 25 wherein the system for automatically reforming the at least one capacitor system initiates a periodic charging of the at least one capacitor system to a minimum voltage less than a full reform voltage and compares a time period for the periodic charging with a predetermined time limit to determine whether to initiate a full reform cycle of the at least one capacitor system.

28. The ICD of claim 25 wherein the system for automatically reforming the at least one capacitor system selectively performs a soft reform of the capacitor system.

29. An implantable cardioverter defibrillator (ICD) comprising a capacitor system having at least two high voltage capacitors which are charged from a battery system by control circuitry integrated within the ICD to deliver an electrical countershock in response to detection of a cardiac dysrhythmia, the capacitor system being automatically reformed by a system within the ICD that selectively isolates the at least two capacitors during reforming using electronic switches to charge only one capacitor at a time.

30. The ICD of claim 29 wherein the system which automatically reforms the capacitor system also selectively interconnects the at least two capacitors during reforming to transfer residual charge from one capacitor to an other capacitor to decrease an amount of energy otherwise required to charge the other capacitor.

* * * * *